(12) United States Patent
Moroiwa et al.

(10) Patent No.: US 9,518,007 B2
(45) Date of Patent: Dec. 13, 2016

(54) URETHANE (METH) ACRYLATE COMPOUND

(71) Applicant: JAPAN U-PICA COMPANY, LTD., Tokyo (JP)

(72) Inventors: Tetsuji Moroiwa, Hiratsuka (JP); Nozomi Ishine, Hiratsuka (JP); Hiroshi Hayashi, Hiratsuka (JP)

(73) Assignee: JAPAN U-PICA COMPANY, LTD., Tokyo (JP)

( * ) Notice: Subject to any disclaimer, the term of this patent is extended or adjusted under 35 U.S.C. 154(b) by 0 days.

(21) Appl. No.: 14/763,645

(22) PCT Filed: Jan. 15, 2014

(86) PCT No.: PCT/JP2014/000160
§ 371 (c)(1),
(2) Date: Jul. 27, 2015

(87) PCT Pub. No.: WO2014/119234
PCT Pub. Date: Aug. 7, 2014

(65) Prior Publication Data
US 2015/0361035 A1    Dec. 17, 2015

(30) Foreign Application Priority Data

Jan. 29, 2013  (JP) ................................. 2013-014694

(51) Int. Cl.
| | | |
|---|---|---|
| C08G 65/32 | (2006.01) |
| C07C 271/08 | (2006.01) |
| C08G 18/67 | (2006.01) |
| C08F 290/06 | (2006.01) |
| C08J 5/04 | (2006.01) |
| C07C 269/02 | (2006.01) |
| C08G 71/04 | (2006.01) |
| C08L 63/10 | (2006.01) |
| C08L 75/16 | (2006.01) |
| C08F 283/06 | (2006.01) |

(52) U.S. Cl.
CPC ........... *C07C 271/08* (2013.01); *C07C 269/02* (2013.01); *C08F 290/068* (2013.01); *C08G 18/672* (2013.01); *C08G 71/04* (2013.01); *C08J 5/042* (2013.01); *C08L 63/10* (2013.01); *C08L 75/16* (2013.01); *C08J 2375/16* (2013.01); *C08L 2312/04* (2013.01)

(58) Field of Classification Search
CPC .................................................. C07C 271/08
USPC ......................................................... 525/397
See application file for complete search history.

(56) References Cited

U.S. PATENT DOCUMENTS

| | | |
|---|---|---|
| 2002/0150755 A1 | 10/2002 | Kobayashi et al. |
| 2004/0044145 A1 | 3/2004 | Sugimoto et al. |
| 2006/0079660 A1 | 4/2006 | Ludewig et al. |
| 2007/0099115 A1 | 5/2007 | Umemoto |
| 2007/0232751 A1 | 10/2007 | Ludewig et al. |
| 2008/0125546 A1 | 5/2008 | Yamaguchi et al. |
| 2015/0034243 A1* | 2/2015 | Haveman ............. C08G 18/329 156/331.1 |

FOREIGN PATENT DOCUMENTS

| | | |
|---|---|---|
| CA | 2015476 C | 10/1990 |
| DE | 690 03 592 T2 | 5/1991 |
| DE | 10 2010 001 956 A1 | 8/2010 |
| EP | 0318616 A1 | 6/1989 |
| JP | 62-292839 A | 12/1987 |
| JP | 63-265931 A | 11/1988 |
| JP | 3-33270 A | 2/1991 |
| JP | 11-200252 A | 7/1999 |
| JP | 2001-40061 A | 2/2001 |
| JP | 2006-111876 A | 4/2006 |
| JP | 2007-277554 A | 10/2007 |

OTHER PUBLICATIONS

International Preliminary Report on Patentability and English translation of the Written Opinion of the International Searching Authority (Forms PCT/IB/373 and PCT/ISA/237), dated Aug. 4, 2015, for International Application No. PCT/JP2014/000160.

Lipatov et al., "Effect of Small Oligomer Additives on the Viscoelastic Properties of Carbon Fibre Plastics," Mechanics of Composite Materials, vol. 29, No. 4, 1993, pp. 440-445, with English abstract.

Lipatova et al., "Electrochemical Polymerization of Unsaturated Isocyanate on the Surface of Carbon Fibers," Vysokomolekulyarnye Soedineniya, vol. 28, No. 10, pp. 2043-2049, with English summary.

(Continued)

*Primary Examiner* — Terressa Boykin
(74) *Attorney, Agent, or Firm* — Birch, Stewart, Kolasch & Birch, LLP

(57) ABSTRACT

The present invention provides a thermosetting resin which enables the production of a carbon fiber reinforced plastic having a good workability and excellent mechanical properties by hand lay up (HUP) molding, resin transfer molding (RTM) or vacuum assisted resin transfer molding (VaRTM). The urethane (meth) acrylate compound (A) according to the present invention is an urethane (meth) acrylate produced by reacting a compound having two or more isocyanate groups with a monoalcohol compound containing ethylenically unsaturated groups or by reacting a compound having two or more isocyanate groups with a monoalcohol compound containing ethylenically unsaturated groups and an alcohol compound having two or more hydroxyl groups, said urethane (meth) acrylate compound (A) being characterized by having an isocyanate group and ethylenically unsaturated groups.

11 Claims, 1 Drawing Sheet

(56) References Cited

OTHER PUBLICATIONS

Matyushova et al., "Electroinitiated polymerization of aliphatic isocyanate-containing oligomer in the presence of carbon fibres," Ukrainskii Khimicheskii Zhurnal, 1988, vol. 54, No. 11, pp. 1213-1216.

Thomas et al., "Improvement of Fibre/Matrix Bonding in Carbon-Fibre/Acrylic Composites by Electron-Irradiation: Concept of Difunctional Chemical Coupling Agent," Composites Science and Technology, vol. 52, 1994, pp. 299-307.

Thomas et al., "Synthesis of (6-isocyanato n-hexyl)carbamoyloxyethylmethacrylate and its uses as sizing-agent for carbon fiber composite materials cured by electron beam," Polymer Bulletin, Sep. 1992, vol. 29, No. 3/4, pp. 259-264.

Extended European Search Report, issued Jun. 6, 2016, for European Application No. 14746050.5.

Lipatova et al., "Electrochemical Polymerization of an Unsaturated Isocyanate on the Surface of Carbon Fibres," Polymer Science U.S.S.R., vol. 28, No. 10, 1986, pp. 2267-2275.

* cited by examiner

URETHANE (METH) ACRYLATE COMPOUND

TECHNICAL FIELD

The present invention relates to a urethane (meth) acrylate compound, and a urethane (meth) acrylate resin by using the compound.

BACKGROUND ART

Since a carbon fiber reinforced plastic is lightweight and high-strength, it is used in various fields such as a member of airplane or automobile, a concrete reinforcing material, a sporting gear etc. In particular, since a demand for a weight saving of a member of airplane or automobile has recently been growing because of concerns about energy issues, a ratio of using a carbon fiber reinforced plastic is increasing.

As a method for producing these carbon fiber reinforced plastics, mention may be made of an autoclave molding of laminating a sheet which an epoxy resin is preliminarily impregnated and thereby bagging them and molding them at autoclave by applying temperature and pressure, a compression molding using a prepreg sheet, and a filament winding (FW) molding of impregnating and rewinding a temperature controlled resin. The autoclave molding makes it possible to give a pressure uniformly to obtain parts having a complicated shape. However, since there are some problems that it needs a long cure time, and the use of the autoclave or a special kind of subsidiary material, an improvement is required. Since the compression molding requires a mold, it is difficult to apply many kinds of small quantities production, and a shape produced by FW molding is limited. In order to solve these problems, a RTM (Resin Transfer Molding) or VaRTM (Vacuum assisted Resin Transfer Molding) methods wherein a dry preform of carbon fibers is set into a mold to inject an epoxy resin to heat and cure, are recently developed. However, there are still problems that a heating of resin during injection is required, or a cure time is long, or a cure at a high temperature is required, or a lifetime of a mold is short or a residual void exists. Moreover, in the case that unsaturated polyester resin wherein it has a good performance in a glass fiber reinforced plastics, a molding time is short, and a workability and a hardenability is superior, is applied as a matrix of a carbon fiber reinforced plastic, although a formability is good, but in the present circumstances it is impossible to obtain sufficient mechanical properties.

It is known that urethane (meth) acrylate has superior adhesion properties to carbon fibers historically, it is used as a sizing agent of carbon fibers (For example, Patent literature 1).

Moreover, it is suggested that since urethane (meth) acrylate has a good adhesion properties to a reinforced fiber, it can be used by mixing it with a resin having inferior adhesion properties to a reinforced fiber (For example, Patent Literature 2).

PRIOR ART LITERATURE

Patent Literatures

Patent literature 1: JP-A-H11-200252
Patent literature 2: JP-A-S62-292839

DISCLOSURE OF THE INVENTION

Problems to be Resolved by the Invention

However, in the above patent literatures 1 and 2, isocyanate groups in the urethane (meth) acrylate are not mentioned.

Therefore, it is an object of the present invention to provide a thermosetting resin capable of producing a carbon fiber reinforced plastic having a good workability and superior mechanical properties by a hand lay-up (HUP) molding, a resin transfer molding (RTM) and a Vacuum assisted resin transfer molding (VaRTM).

Means of Solving the Problems

The present inventors made strenuous studies. As a result, the inventors discovered that a urethane (meth) acrylate resin having isocyanate groups and ethylenically unsaturated groups make it possible to produce a carbon fiber reinforced plastic having a good workability and superior mechanical properties as a matrix of carbon fibers.

That is, a urethane (meth) acrylate compound (A) according to the present invention is characterized in that it is represented by the following chemical formula [Chemical 1]:

$$X\text{-}[M]_n \qquad \text{[Chemical 1]}$$

(wherein X is a compound residue having two or more isocyanate groups, M contains at least the following formula [Chemical 2]:

$$-\text{NCO} \qquad \text{[Chemical 2]}$$

and M other than the above formula [Chemical 2] is the following formula [Chemical 3]:

[Chemical 3]

Q is a monoalcohol compound residue containing ethylenically unsaturated groups in the formula. An "n" is 2 to 7.).

Furthermore, a urethane (meth) acrylate compound (A) according to the present invention is characterized in that it is represented by the following chemical formula [Chemical 4]:

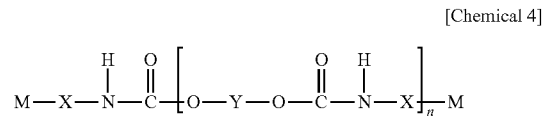
[Chemical 4]

(wherein X is a compound residue having two or more isocyanate groups, Y is an alcohol compound residue having two or more hydroxyl groups, M contains at least the following formula [Chemical 5]:

$$-\text{NCO} \qquad \text{[Chemical 5]}$$

and M other than the above formula [Chemical 5] is the following formula [Chemical 6]:

[Chemical 6]

Q is a monoalcohol compound residue containing ethylenically unsaturated groups in the formula. An "n" is 1 to 5000.).

Furthermore, a urethane (meth) acrylate compound (A) according to the present invention is characterized in that it is a urethane (meth) acrylate produced by reacting a compound having two or more isocyanate groups with a monoalcohol compound containing ethylenically unsaturated groups or by reacting a compound having two or more isocyanate groups with a monoalcohol compound containing ethylenically unsaturated groups and an alcohol compound having two or more hydroxyl groups, the urethane (meth) acrylate compound (A) being characterized by having isocyanate groups and ethylenically unsaturated groups.

Furthermore, in a preferred embodiment of the urethane (meth) acrylate compound (A) according to the present invention, the compound is characterized in that isocyanate groups existing in the urethane (meth) acrylate compound (A) are at 0.1 to 12 percent by weight.

Furthermore, in a preferred embodiment of the urethane (meth) acrylate compound (A) according to the present invention, the compound is characterized in that the alcohol compound having two or more hydroxyl groups is one or more selected from 1,3-propanediol, 1,4-butanediol, 1,5-pentanediol, 1,6-hexanediol.

Furthermore, in a preferred embodiment of the urethane (meth) acrylate compound (A) according to the present invention, the compound is characterized in that the alcohol compound having two or more hydroxyl groups is polyester polyol obtained by the polycondensation of dicarboxylic acid or an ester forming derivative thereof with glycol.

Furthermore, in a preferred embodiment of the urethane (meth) acrylate compound (A) according to the present invention, the compound is characterized in that the alcohol compound having two or more hydroxyl groups is polyester polyol obtained by the polycondensation of one or more selected from terephthalic acid, isophthalic acid, an ester forming derivative thereof, with one or more selected from 1,3-propanediol, 1,4-butanediol, 1,5-pentanediol, 1,6-hexanediol.

Furthermore, in a preferred embodiment of the urethane (meth) acrylate compound (A) according to the present invention, the compound is characterized in that the compound having two or more isocyanate groups is one or more selected from 1,6-hexamethylene diisocyanate, 1,3-bis (isocyanatomethyl) cyclohexane, isophorone diisocyanate, and a prepolymer thereof, polymethylenepolyphenyl polyisocyanate.

Furthermore, the urethane (meth) acrylate resin (B) according to the present invention is characterized in that it comprises the urethane (meth) acrylate compound (A) according to the present invention and a polymerizable monomer.

Furthermore, in a preferred embodiment of the urethane (meth) acrylate resin (B) according to the present invention, the resin is characterized in that isocyanate groups existing in the urethane (meth) acrylate resin (B) is at 0.1 to 8 percent by weight.

Furthermore, a resin composition for a carbon fiber reinforced plastic according to the present invention is characterized in that it comprises the urethane (meth) acrylate compound (A) according to the present invention and a thermosetting resin having ethylenically unsaturated groups, and it contains isocyanate groups at 0.1 to 8 percent by weight in the resin composition.

Effect of Invention

The present invention has an advantage effect that it is possible to provide a thermosetting resin used for a carbon fiber reinforced plastic having properties such as a light-weight or a high-strength. Further, the present invention has an advantage effect that since it can obtain a carbon fiber reinforced plastic having a superior workability and mechanical properties (a flexural strength, a compressive strength, an interlaminar shear strength), it is possible to apply a carbon fiber reinforced plastic to various fields.

MODE FOR CARRYING OUT THE INVENTION

Figure 1:
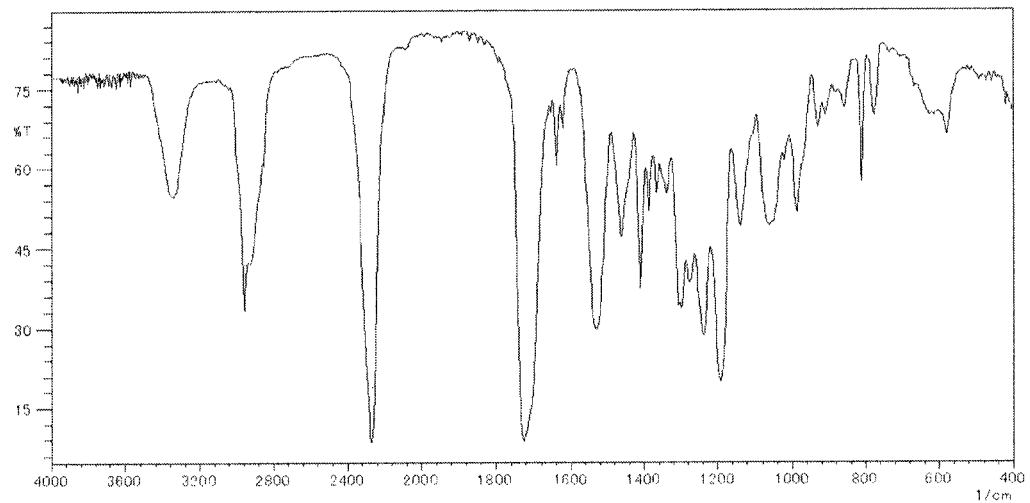
FIG. 1 gives an IR spectrum of urethane (meth) acrylate resin compound (A) having isocyanate groups and ethylenically unsaturated groups in one embodiment of the present invention (which is those having a basic structure of [Chemical 1]. The absorption of isocyanate groups at about 2250 $cm^{-1}$ can be confirmed.
Figure 2:
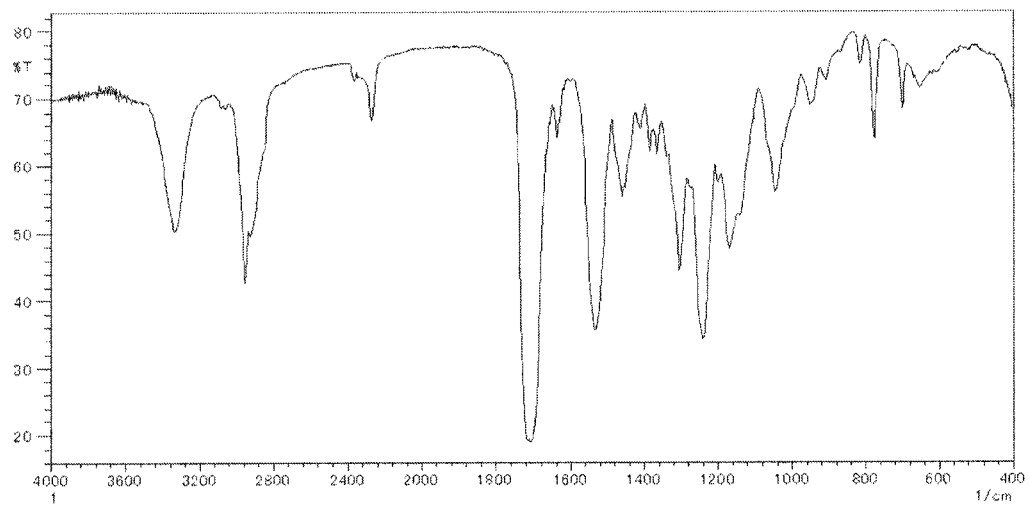
FIG. 2 gives an IR spectrum of urethane (meth) acrylate resin compound (A) having isocyanate groups and ethylenically unsaturated groups in one embodiment of the present invention (which is those having a basic structure of [Chemical 4]). The absorption of isocyanate groups at about 2250 $cm^{-1}$ can be confirmed.
Figure 3:
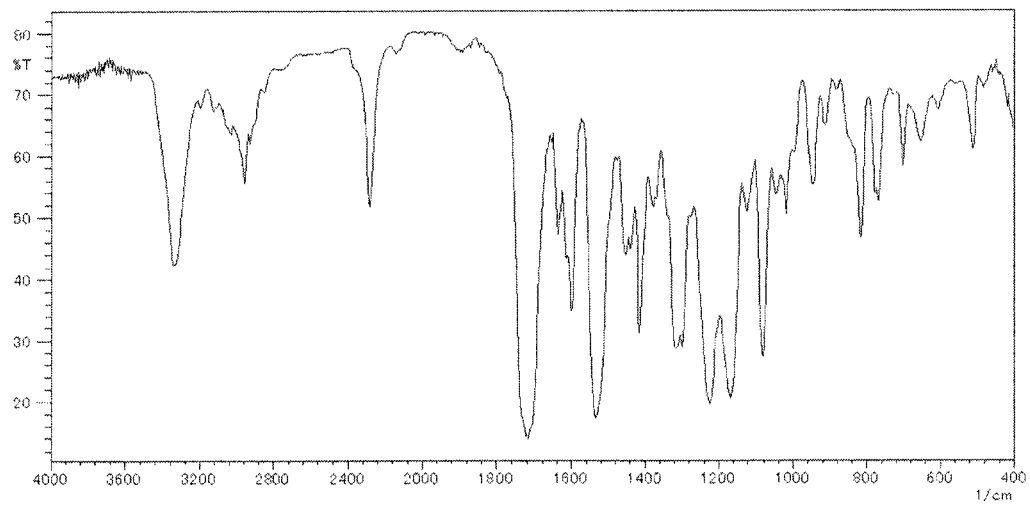
FIG. 3 gives an IR spectrum of urethane (meth) acrylate resin compound (A) having isocyanate groups and ethylenically unsaturated groups in one embodiment of the present invention (which is those of the synthetic example 10 as described later in the Example (which is those that the compound having two or more isocyanate groups is polymethylenepolyphenyl polyisocyanate.). The absorption of isocyanate groups at about 2250 $cm^{-1}$ can be confirmed.

In the present invention, urethane (meth) acrylate means urethane methacrylate and urethane acrylate, in a similar way, (meth) acrylic ester means methacrylic ester and acrylic ester.

A urethane (meth) acrylate compound (A) according to the present invention is characterized in that it is represented by the following chemical formula [Chemical 7]:

$$X \!\!-\!\![M]_n \quad \text{[Chemical 7]}$$

(wherein X is a compound residue having two or more isocyanate groups, M contains at least the following formula [Chemical 8]:

$$\text{—NCO} \quad \text{[Chemical 8]}$$

and M other than the above formula [Chemical 8] is the following formula [Chemical 9]:

[Chemical 9]

Q is a monoalcohol compound residue containing ethylenically unsaturated groups in the formula. An "n" is 2 to 7.).

Furthermore, a urethane (meth) acrylate compound (A) according to the present invention is characterized in that it is represented by the following chemical formula [Chemical 10]:

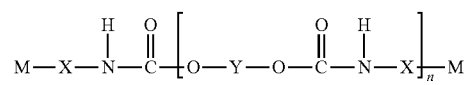

[Chemical 10]

(wherein X is a compound residue having two or more isocyanate groups, Y is an alcohol compound residue having two or more hydroxyl groups, M contains at least the following formula [Chemical 11]:

 [Chemical 11]

and M other than the above formula [Chemical 11] is the following formula [Chemical 12]:

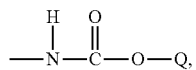 [Chemical 12]

Q is a monoalcohol compound residue containing ethylenically unsaturated groups in the formula. An "n" is 1 to 5000.).

In the present invention, it is possible to obtain the compound described in the above [Chemical 1] by reacting with a compound having two or more isocyanate groups and a monoalcohol compound containing ethylenically unsaturated groups.

Furthermore, in the present invention, it is possible to obtain the compound described in the above [Chemical 4] by reacting with a compound having two or more isocyanate groups and a monoalcohol compound containing ethylenically unsaturated groups and an alcohol compound having two or more hydroxyl groups.

A urethane (meth) acrylate compound (A) having isocyanate groups and ethylenically unsaturated groups produced by reacting a compound having two or more isocyanate groups with a monoalcohol compound containing ethylenically unsaturated groups, or by reacting a compound having two or more isocyanate groups with a monoalcohol compound containing ethylenically unsaturated groups and an alcohol compound having two or more hydroxyl groups, and a urethane (meth) acrylate resin (B) comprising a urethane (meth) acrylate compound (A) having isocyanate groups and ethylenically unsaturated groups and a polymerizable monomer may be explained.

A urethane (meth) acrylate compound (A) having isocyanate groups and ethylenically unsaturated groups can be obtained by reacting a compound having two or more isocyanate groups with a monoalcohol compound containing ethylenically unsaturated groups, or by reacting a compound having two or more isocyanate groups with a monoalcohol compound containing ethylenically unsaturated groups and an alcohol compound having two or more hydroxyl groups. At this time, it may react so that the number of moles of isocyanate groups in an isocyanate compound could be more than the number of moles of all hydroxyl groups in a monoalcohol compound containing ethylenically unsaturated groups and an alcohol compound having two or more hydroxyl groups. It is preferable that this reaction may be carried out by the time an amount of a remaining isocyanate group becomes constant, in other wards by the time a hydroxyl group is almost consumed.

The urethane (meth) acrylate compound (A) obtained thus has preferably 0.1 to 12 percent by weight of isocyanate groups. Further, it has preferably 0.3 to 12 percent by weight of isocyanate groups. There is possibility that in the case that the isocyanate group is less than 0.1 percent by weight, the adhesion with carbon fibers is inferior, a compressive strength and an interlaminar shear strength are not sufficiently obtained, in the case that it is more than 12 percent by weight, a flexural strength and a tensile strength reduce and a balance of mechanical properties is lost.

As an isocyanate compound having two or more isocyanate groups used for the present invention, for example, mention may be made of an aromatic isocyanate compound such as 1,3-xylylene diisocyanate, 2,4-tolylene diisocyanate, 2,6-tolylene diisocyanate, 4,4'-diphenyl diisocyanate, 1,5-naphthylene diisocyanate, 4,4'-diphenyl methane diisocyanate, polymethylene polyphenyl polyisocyanate, m-tetramethyl xylene diisocyanate, an alicyclic isocyanate compound such as hydrogenated 1,3-xylylene diisocyanate, (1,3-bis (isocyanatomethyl) cyclohexane), isophorone diisocyanate, norbornene diisocyanate, hydrogenated 4,4'-diphenyl methane diisocyanate (4,4'-dicyclohexylmethan diisocyanate), 1,4-cyclohexane diisocyanate, an aliphatic isocyanate compound such as 1,6-hexamethylene diisocyanate, trimethylene diisocyanate, trifunctional isocyanate having an isocyanurate ring wherein a difunctional isocyanate compound is trimerized, isocyanate prepolymer etc., which is modified by a commercially available polyol. These isocyanate compounds may be used by itself or by the combination of two or more thereof.

Furthermore, among these isocyanate compound, from a viewpoint of a heat resistance and a light stability, 1,6-hexamethylene diisocyanate, 1,3-bis (isocyanatomethyl) cyclohexane, isophorone diisocyanate and a prepolymer thereof, polymethylene polyphenyl polyisocyanate are particularly preferable.

As an alcohol compound having two or more hydroxyl group, mention may be made of an aliphatic alcohol, an etherified diphenol, a polyester polyol etc.

As an aliphatic alcohol, for example, mention may be made of ethylene glycol, 1,2-propanediol, 1,3-propanediol, 1,2-butanediol, 1,3-butanediol, 1,4-butanediol, 2,3-butanediol, 1,4-butenediol, 2-methyl-1,3-propanediol, 1,5-pentanediol, neopentyl glycol, 2-ethyl-2-methylpropane-1,3-diol, 2-butyl-2-ethylpropane-1,3-diol, 1,6-hexanediol, 3-methyl-1,5-pentanediol, 2-ethyl-1,3-hexanediol, 2,4-dimethyl-1,5-pentanediol, 2,2,4-trimethyl-1,3-pentanediol, 1,7-heptanediol, 1,8-octanediol, 1,9-nonanediol, 1,10-decanediol, diethylene glycol, triethylene glycol, dipropylene glycol, polypropylene glycol, polyethylene glycol etc. As an alicyclic alcohol, mention may be made of hydrogenated bisphenol A, tricyclodecane dimethanol, spiroglycol etc. Among the aliphatic alcohol compound, from a viewpoint of a viscosity of resin and mechanical properties of a cured material, 1,3-propanediol, 1,4-butanediol, 1,5-pentanediol, 1,6-hexanediol are preferable.

As the etherified diphenol, for example, mention may be made of a diol obtained by the addition reaction of bisphenol A with alkylene oxide, and a diol obtained by brominating an additive of bisphenol A and alkylene oxide etc. As the alkylene oxide, mention may be made of ethylene oxide or propylene oxide, those wherein the average number of added moles of the alkylene oxide is 2 to 16 moles for 1 mole of bisphenol A, is preferable.

As the polyester polyol, mention may be made of those of the polycondensation of unsaturated acid and/or saturated acid with the aliphatic alcohol and the etherified diphenol. As the unsaturated acid, mention may be made of maleic anhydride, maleic acid, and fumaric acid, as the saturated acid, mention may be made of phthalic acid, terephthalic acid, isophthalic acid, 1,4-cyclohexanedicarboxylic acid, adipic acid, succinic acid, sebacic acid, alkyl succinic acid, alkenyl succinic acid, itaconic acid, biphenyldicarboxylic acid, naphthalenedicarboxylic acid, 5-tert-butyl-1,3-benzenedicarboxylic acid and acid anhydride thereof, and an ester forming derivative such as a lower alkyl ester, acid halide etc. As a particularly preferable dicarboxylic acid, mention may be made of terephthalic acid and isophthalic acid. As terephthalic acid and isophthalic acid, a lower alkyl ester thereof may be used, for example, although mention may be made of dimethyl terephthalate, dimethyl isophthalate, diethyl terephthalate, diethyl isophthalate, dibutyl terephthalate, dibutyl isophthalate, from a viewpoint of a cost and a handling, dimethyl terephthalate or dimethyl isophthalate is preferable. It is possible to use a lower alkyl ester of terephthalic acid and isophthalic acid, as an example of a lower alkyl ester of terephthalic acid and isophthalic acid, although mention may be made of dimethyl terephthalate, dimethyl isophthalate, diethyl terephthalate, diethyl isophthalate, dibutyl terephthalate, dibutyl isophthalate, it is preferable to be dimethyl terephthalate or dimethyl isophthalate, from a viewpoint of a cost and a handling. These unsaturated acid and saturated acid may be used by itself or by the combination of two or more thereof.

Furthermore, in a preferred embodiment of the urethane (meth) acrylate compound (A) according to the present invention, the alcohol compound having two or more hydroxyl groups is polyester polyol obtained by the polycondensation of dicarboxylic acid or an ester forming derivative thereof with glycol. As the polyester polyol, from a viewpoint of a viscosity of resin and mechanical properties of a cured material, a polyester polyol is particularly preferable which is obtained by the polycondensation of one or more selected from terephthalic acid and isophthalic acid and an ester forming derivative thereof with 1,3-propanediol, 1,4-butanediol, 1,5-pentanediol, 1,6-hexanediol. These alcohol compounds may be used by itself or by the combination of two or more thereof. Further, it is also possible to use a trivalent or more of polyol without degrading an effect of the present invention. As a trivalent or more of polyol, mention may be made of glycerin, trimethylolethane, trimethylolpropane, pentaerythritol etc., and these may be used by itself or by the combination of two or more thereof.

A monoalcohol compound containing ethylenically unsaturated groups means (meth) acrylic ester containing a hydroxyl group, for example, mention may be made of, 2-hydroxyethyl (meth) acrylate, 3-hydroxypropyl (meth) acrylate, 4-hydroxybutyl (meth) acrylate, polyethylene glycol mono (meth) acrylate, trimethylolpropane di (meth) acrylate, pentaerythritol tri (meth) acrylate, dipentaerythritol penta (meth) acrylate, diacrylated isocyanurate etc. These monoalcohol compounds containing ethylenically unsaturated groups may be used by itself or by the combination of two or more thereof. Further, among these monoalcohol compound containing ethylenically unsaturated groups, from a viewpoint of a viscosity of resin and mechanical properties of a cured material, 2-hydroxyethyl (meth) acrylate is preferable.

Although a urethane (meth) acrylate compound. (A) according to the present invention can be obtained by reacting a compound having two or more isocyanate groups with a monoalcohol compound containing ethylenically unsaturated groups, or by reacting a compound having two or more isocyanate groups with a monoalcohol compound containing ethylenically unsaturated groups and an alcohol compound having two or more hydroxyl groups, as to the reaction temperature, it is preferably reacted at 40 to 140° C., it is more preferably reacted at 70 to 110° C. The terminal point of the reaction can be confirmed by the quantitative determination of the isocyanate group according to the titration, or by the tracking of the absorption (about 2250 cm$^{-1}$) of the isocyanate group by the infrared absorption spectrum (hereinafter, it is omitted as IR).

In the reaction, the known catalyst, a polymerization inhibitor may be used. Although as a catalyst, an acid catalyst and an alkali catalyst may be used, a tin compound such as dibutyltin dilaurate or dibutyltin diacetate is preferable. As to an additive amount of the catalyst, an addition of 100 to 2000 ppm for the total amount in weight is preferable. As a polymerization inhibitor, for example, a polyhydric phenolic polymerization inhibitor such as hydroquinone, parabenzoquinone, methylhydroquinone, trimethylhydroquinone may be used. As to an additive amount of the polymerization inhibitor, an addition of 100 to 2000 ppm for the total amount in weight is preferable. Further, according to needs, it is possible to synthesize it under a system wherein a polymerizable monomer which does not react with the isocyanate group is added.

An equivalent weight of the ethylenically unsaturated group of the urethane (meth) acrylate compound (A) according to the present invention is not particularly limited to, but there is a possibility that in the case that it is 1500 g/eq or more, a balance of mechanical properties (a flexural strength, a tensile strength, a compressive strength, a interlaminar shear strength) becomes worse, and a heat resistance of a molded article goes down. Provided, however, that this shall not apply in the case that it is blended with the other thermosetting resin as mentioned after, and it is blended so that the isocyanate group in the blended resin could be 0.1 to 7 percent by weight.

Furthermore, the urethane (meth) acrylate resin (B) according to the present invention is characterized in that it comprises the urethane (meth) acrylate compound (A) according to the present invention and a polymerizable monomer. At first, the urethane (meth) acrylate resin (B) comprising a urethane (meth) acrylate compound (A) having isocyanate groups and ethylenically unsaturated groups, and a polymerizable monomer may be explained.

As a polymerizable monomer used in the present invention, it is preferably a compound which does not react with isocyanate groups at a room temperature. In the case that a polymerizable monomer capable of reacting with isocyanate groups is blended, there is a possibility that during storage it reacts and thereby a viscosity increasing to make workability worse or it is impossible to obtain sufficient mechanical properties. Mention may be made of a vinyl monomer, a monofunctional acrylic ester, or a polyfunctional acrylic ester. As a vinyl monomer, mention may be made of styrene, vinyl toluene, α-methylstyrene, vinyl acetate, as a monofunctional acrylic ester, mention may be made of methyl methacrylate, benzyl (meth) acrylate, n-butyl (meth) acrylate, i-butyl (meth) acrylate, t-butyl (meth) acrylate, 2-ethylhexyl (meth) acrylate, tetrahydrofurfuryl (meth) acrylate, lauryl (meth) acrylate, tridecyl (meth) acrylate, stearyl (meth) acrylate, 2-methoxyethyl (meth) acrylate, 2-ethoxyethyl (meth) acrylate, cyclohexyl (meth) acrylate, isobornyl (meth) acrylate, norbornyl (meth) acrylate, dicyclopentenyl (meth) acrylate, dicyclopentenyl oxyethyl (meth) acrylate etc., as a polyfunctional acrylic ester, mention may be made of ethylene glycol di (meth) acrylate, 1,3-propanediol di (meth) acrylate, 1,4-butanediol di (meth) acrylate, neopentyl glycol di (meth) acrylate, diethylene glycol di (meth) acrylate, tripropylene di (meth) acrylate, norbornene dimethanol di (meth) acrylate, tricyclodecane dimethanol di (meth) acrylate, propylene oxide additional bisphenol A di (meth) acrylate, trimethylolpropane tri (meth) acrylate, tris (2-(meth) acryloyloxyethyl) isocyanurate etc. These may be suitably used by the combination of two or more thereof. As a polymerizable monomer, from a viewpoint of viscosity of resin and mechanical properties, an application of styrene, methyl methacrylate are preferable.

In a preferred embodiment, in the present invention, a polymerizable monomer is contained so that the percent by weight of isocyanate groups existing in the urethane (meth) acrylate resin (B) could be more than 0 to 8 percent by weight, preferably 0.1 to 8 percent by weight. Further, a polymerizable monomer is preferably contained so that the percent by weight of isocyanate groups existing in the urethane (meth) acrylate resin (B) could be 0.2 to 8 percent by weight. This is because that the existence of a little amount of isocyanate group makes it possible to improve adhesiveness to fibers etc., and to obtain better mechanical properties. For example, it is possible to solve 100 parts by weight of a urethane (meth) acrylate compound (A) to 20 to 200 parts by weight of a polymerizable monomer. Preferably, it is possible to solve 100 parts by weight of a urethane (meth) acrylate compound (A) to 40 to 150 parts by weight of a polymerizable monomer. In the case that an amount of a polymerizable monomer for 100 parts by weight of a urethane (meth) acrylate compound (A) is less than 40 parts by weight, there is a possibility that it becomes extremely high viscosity and thereby a moldability becoming inferior. In the case that an amount of a polymerizable monomer for 100 parts by weight of a urethane (meth) acrylate compound (A) is more than 150 parts by weight, there is a possibility that a performance of the cured molded product obtained thus becomes inferior.

In the case that isocyanate groups existing in the urethane (meth) acrylate resin (B) are less than 0.1 percent by weight, there is a possibility that an adhesion with carbon fibers becomes inferior, it is impossible to obtain a sufficient compressive strength or interlaminar shear strength, in the case that isocyanate groups existing in the urethane (meth) acrylate resin (B) are more than 8 percent by weight, there is a possibility that a flexural strength or a tensile strength reduces to lose a balance of mechanical properties.

In order to apply the present invention to hand lay up (HUP) molding, resin transfer molding (RTM) or vacuum assisted resin transfer molding (VaRTM), a viscosity of the urethane (meth) acrylate resin (B) is preferably 30 to 700 mPa-s (25° C.). In the case that it is less than 30 mPa-s, there is a possibility of resin leaking when it is impregnated to the carbon fibers, in the case that it is more than 700 mPa-s, there is a possibility that a non-impregnated part remains. However, this shall not apply in the case where a viscosity of resin is deliberately lowered or heighten by a temperature control.

As a method of curing of the urethane (meth) acrylate compound (A) and the urethane (meth) acrylate resin (B) according to the present invention, it is possible to apply the same known method as a radical polymerization type of resin of the prior art. Mention may be made of a curing by an organic peroxide, a curing by an ultraviolet initiator, a curing by electron ray. Further, it is possible to add an accelerator or polymerization inhibitor for controlling a cure rate, waxes for adding an air drying property in the same manner as a radical polymerization type of resin in the prior art.

As the organic peroxide type of a curing agent, for example, mention may be made of a ketone peroxide system such as methyl ethyl ketone peroxide, acetylacetone peroxide, a diacyl peroxide system such as benzoyl peroxide, a peroxyester system such as t-butyl peroxy benzoate, a hydro-peroxide system such as cumene hydro-peroxide, a dialkyl peroxide system such as dicumyl peroxide etc. An additive amount of the curing agent is 0.05 to 5 parts by weight for 100 parts by weight of the urethane (meth) acrylate compound (A) and the urethane (meth) acrylate resin (B).

As the ultraviolet initiator, for example, mention may be made of a benzophenone system such as benzophenone, benzyl, methyl ortho benzoyl benzoate, a benzoin ether system such as benzoin alkyl ether, an acetophenone system such as benzyl dimethyl ketal, 2,2-diethoxy acetophenone, 2-hydroxy-2-methylpropiophenone, 4-isopropyl-2-hydroxyl-2-methylpropiophenone, 1,1-dichloroacetophenone, a thioxanthone system such as 2-chlorothioxanthone, 2-methylthioxanthone, 2-isopropylthioxanthone. An additive amount of the ultraviolet initiator is 0.1 to 5 parts by weight for 100 parts by weight of unsaturated polyester resin.

As a curing accelerator, for example, mention may be made of metal soaps such as cobalt naphthenate, cobalt octoate, zinc octoate, vanadium octoate, copper naphthenate, barium naphthenate, metal chelates such as vanadium acetylacetonate, cobalt acetylacetonate, iron acetylacetonate, tertiary amines such as N, N-dimethylaniline, N, N-diethylaniline, N, N-dimethyl-p-toluidine, 4-(N, N-dimethylamino) benzaldehyde, pyridine, phenylmorpholine etc. An additive amount of the curing accelerator is 0.05 to 5 parts by weight.

Furthermore, a resin composition for carbon fibers reinforced plastic according to the present invention is characterized in that it comprises the urethane (meth) acrylate compound (A) according to the present invention and a thermosetting resin having ethylenically unsaturated groups, and it contains isocyanate groups at 0.1 to 8 percent by weight in the resin composition.

It is possible to blend and use other thermosetting resin having ethylenically unsaturated groups with the urethane (meth) acrylate compound (A) and the urethane (meth) acrylate resin (B) according to the present invention. A thermosetting resin means, for example, an unsaturated polyester resin, an epoxy (meth) acrylate resin, a urethane (meth) acrylate resin, it is preferable that any of them is blended so that an isocyanate group existing the blend resin could be 0.1 to 8 percent by weight, from a viewpoint of adhesion to carbon fibers. Further, in the case that it is blended with an unsaturated polyester resin or an epoxy (meth) acrylate resin having a hydroxyl group or a carboxyl group, from a viewpoint of stability in storage, a blending just before molding is desirable.

It is also possible to apply the resin composition for a carbon fiber reinforced plastic according to the present invention to a reinforced plastic with reinforced fibers other than the carbon fibers. Although as reinforced fibers other than the carbon fibers, mention may be made of glass fibers, aramid fibers, zylon fibers, vinylon fibers, polyethylene fibers, boron fibers, basalt fibers, cellulose etc., but it is not limited to those.

EXAMPLE

The present invention will be concretely explained in more detail with reference to Examples below. The invention is not intended to be interpreted as being limited to Examples. In the present Examples, the "parts" shows parts by weight if not otherwise specified.

A content of the isocyanate group in the synthesis examples was measured by solving each resins to a dry toluene and after that adding an excessive di-n-butylamine solution to react, and thereby a back titration of a remaining di-n-butylamine being carried out by using hydrochloric acid.

Synthesis Example 1

A reaction vessel equipped with a gas introduction tube, a stirring device, a condenser, a thermometer, was charged with 404 parts of isophorone diisocyanate (Evonik Co., Ltd) and 0.13 parts of dibutyltin dilaurate, then a mixture solution of 76 parts of 1,3-propanediol (Du Pont Kabushiki Kaisha), 169 parts of 2-hydroxyethyl methacrylate (Mitsubishi Gas Chemical Co., Inc.) and 0.32 parts of monomethyl ether hydroquinone was dropped for 40 minutes with stirring, under air atmosphere and heating condition. The temperature was maintained at 85 to 95° C. to react. The reaction was traced by an infrared absorption spectrometry and the end point was determined by the constant absorption of an isocyanate group (at about 2250 cm$^{-1}$). A time taken to terminate the reaction was 3 hours. The content of the isocyanate group existing in the urethane (meth) acrylate before it is diluted by a polymerizable monomer was 2.10% by weight, an equivalent weight of an ethylenically unsaturated group was 500 g/eq. After that, it was diluted by 350 parts of a styrene monomer to obtain a urethane (meth) acrylate resin containing 1.37% by weight of the isocyanate group (a-1).

Synthesis Example 2

The same system as the synthesis example 1, was charged with 394 parts of isophorone diisocyanate and 0.13 parts of dibutyltin dilaurate, then a mixture solution of 86 parts of 1,4-butanediol (Mitsubishi Chemical Corporation) 169 parts of 2-hydroxyethyl methacrylate and 0.32 parts of monomethyl ether hydroquinone was dropped for 40 minutes with stirring, under air atmosphere and heating condition. The temperature was maintained at 85 to 95° C. to react. The reaction was traced by an infrared absorption spectrometry and the end point was determined by the constant absorption of an isocyanate group (at about 2250 cm$^{-1}$). A time taken to terminate the reaction was 3 hours. The content of the isocyanate group existing in the urethane (meth) acrylate before it is diluted by a polymerizable monomer was 2.11% by weight, an equivalent weight of an ethylenically unsaturated group was 500 g/eq. After that, it was diluted by 350 parts of a styrene monomer to obtain a urethane (meth) acrylate resin containing 1.37% by weight of the isocyanate group (a-2).

Synthesis Example 3

A stainless-steal reaction vessel equipped with a stirring device, a heating device, a thermometer, a fractionally distilling equipment, a nitrogen gas introduction tube, was charged with 687 parts of dimethyl terephthalate, 539 parts of 1,3-propanediol, then an ester exchange reaction was proceeded under nitrogen atmosphere, with stirring at 200° C., for 5 hours to obtain 138 g/eq of an equivalent weight of hydroxyl group of polyester polyol (P-1). Next, the same system as the synthesis example 1, was charged with 314 parts of isophorone diisocyanate and 0.13 parts of dibutyltin dilaurate, then a mixture solution of 166 parts of polyester polyol (P-1), 169 parts of 2-hydroxyethyl methacrylate, 217 parts of a styrene monomer and 0.32 parts of monomethyl ether hydroquinone was dropped for 40 minutes with stirring, under air atmosphere and heating condition. The temperature was maintained at 85 to 95° C. to react. The reaction was traced by an infrared absorption spectrometry and the end point was determined by the constant absorption of an isocyanate group (at about 2250 cm$^{-1}$). A time taken to terminate the reaction was 3 hours. The content of the isocyanate group existing in the urethane (meth) acrylate before it is diluted by a polymerizable monomer was 2.09% by weight, an equivalent weight of an ethylenically unsaturated group was 500 g/eq. After that, it was diluted by 133 parts of a styrene monomer to obtain a urethane (meth) acrylate resin containing 1.36% by weight of the isocyanate group (a-3).

Synthesis Example 4

The same system as the synthesis example 1, was charged with 206 parts of hexamethylene diisocyanate and 0.13 parts of dibutyltin dilaurate, then a mixture solution of 417 parts of tetrabromo bisphenol-A (2-hydroxyethyl ether) (Meisei chemical works Ltd.), 96 parts of 2-hydroxyethyl methacrylate, 0.32 parts of monomethyl ether hydroquinone and 240 parts of a styrene monomer was dropped for 40 minutes with stirring, under air atmosphere and heating condition. The temperature was maintained at 85 to 95° C. to react. The reaction was traced by an infrared absorption spectrometry and the end point was determined by the constant absorption of an isocyanate group (at about 2250 cm$^{-1}$). A time taken to terminate the reaction was 3 hours. The content of the isocyanate group in the urethane (meth) acrylate was 2.31% by weight, an equivalent weight of an ethylenically unsaturated group was 977 g/eq. After that, it was diluted by 40 parts of a styrene monomer to obtain a urethane (meth) acrylate resin containing 1.66% by weight of the isocyanate group (a-4).

Synthesis Example 5

The same system as the synthesis example 1, was charged with 396 parts of isophorone diisocyanate and 0.13 parts of dibutyltin dilaurate, then a mixture solution of 85 parts of 1,3-propanediol, 169 parts of 2-hydroxyethyl methacrylate and 0.32 parts of monomethyl ether hydroquinone was dropped for 40 minutes with stirring, under air atmosphere and heating condition. The temperature was maintained at 85 to 95° C. to react. The reaction was traced by an infrared absorption spectrometry and the end point was determined by the constant absorption of an isocyanate group (at about 2250 cm$^{-1}$). A time taken to terminate the reaction was 3 hours. The content of the isocyanate group existing in the urethane (meth) acrylate before it is diluted by a polymerizable monomer was 0.21% by weight, an equivalent weight of an ethylenically unsaturated group was 500 g/eq. After that, it was diluted by 350 parts of a styrene monomer to obtain a urethane (meth) acrylate resin containing 0.14% by weight of the isocyanate group (a-5).

Synthesis Example 6

The same system as the synthesis example 1, was charged with 425 parts of isophorone diisocyanate and 0.13 parts of dibutyltin dilaurate, then a mixture solution of 55 parts of 1,3-propanediol, 169 parts of 2-hydroxyethyl methacrylate and 0.32 parts of monomethyl ether hydroquinone was dropped for 40 minutes with stirring, under air atmosphere and heating condition. The temperature was maintained at 85 to 95° C. to react. The reaction was traced by an infrared absorption spectrometry and the point was determined by the constant absorption of an isocyanate group (at about 2250 cm$^{-1}$). A time taken to terminate the reaction was 3 hours. The content of the isocyanate group existing in the urethane (meth) acrylate before it is diluted by a polymerizable monomer was 6.85% by weight, an equivalent weight of an ethylenically unsaturated group was 500 g/eq. After that, it was diluted by 350 parts of a styrene monomer to obtain a urethane (meth) acrylate resin containing 4.45% by weight of the isocyanate group (a-6).

Synthesis Example 7

The same system as the synthesis example 1, was charged with 445 parts of isophorone diisocyanate and 0.13 parts of dibutyltin dilaurate, then a mixture solution of 35 parts of 1,3-propanediol, 169 parts of 2-hydroxyethyl methacrylate and 0.32 parts of monomethyl ether hydroquinone was dropped for 40 minutes with stirring, under air atmosphere and heating condition. The temperature was maintained at 85 to 95° C. to react. The reaction was traced by an infrared absorption spectrometry and the end point was determined by the constant absorption of an isocyanate group (at about 2250 cm$^{-1}$). A time taken to terminate the reaction was 3 hours. The content of the isocyanate group existing in the urethane (meth) acrylate before it is diluted by a polymerizable monomer was 11.59% by weight, an equivalent weight of an ethylenically unsaturated group was 500 g/eq. After that, it was diluted by 350 parts of a styrene monomer to obtain a urethane (meth) acrylate resin containing 7.53% by weight of the isocyanate group (a-7).

Synthesis Example 8

The same system as the synthesis example 1, was charged with 333 parts of 1,3-bis (isocyanatomethyl) cyclohexane (Takeda Pharmaceutical Company Limited) and 0.13 parts of dibutyltin dilaurate, then a mixture solution of 37 parts of 1,3-propanediol, 279 parts of 2-hydroxyethyl methacrylate and 0.32 parts of monomethyl ether hydroquinone was dropped for 40 minutes with stirring, under the condition of blowing air and heating. The temperature was maintained at 85 to 95° C. to react. The reaction was traced by an infrared absorption spectrometry and the end point was determined by the constant absorption of an isocyanate group (at about 2250 cm$^{-1}$). A time taken to terminate the reaction was 3 hours. The content of the isocyanate group existing in the urethane (meth) acrylate before it is diluted by a polymerizable monomer was 2.06% by weight, an equivalent weight of an ethylenically unsaturated group was 300 g/eq. After that, it was diluted by 350 parts of a styrene monomer to obtain a urethane (meth) acrylate resin containing 1.34% by weight of the isocyanate group (a-8).

Synthesis Example 9

The same system as the synthesis example 1, was charged with 411 parts of 2,5-bis (isocyanatomethyl) bicycle [2.2.1] heptane (Takeda Pharmaceutical Company Limited) and 0.13 parts of dibutyltin dilaurate, then a mixture solution of 127 parts of 1,4-butanediol, 112 parts of 2-hydroxyethyl methacrylate and 0.32 parts of monomethyl ether hydroquinone was dropped for 40 minutes with stirring, under air atmosphere and heating condition. The temperature was maintained at 85 to 95° C. to react. The reaction was traced by an infrared absorption spectrometry and the end point was determined by the constant absorption of an isocyanate group (at about 2250 cm$^{-1}$). A time taken to terminate the reaction was 3 hours. The content of the isocyanate group existing in the urethane (meth) acrylate before it is diluted by a polymerizable monomer was 1.94% by weight, an equivalent weight of an ethylenically unsaturated group was 758 g/eq. After that, it was diluted by 350 parts of a styrene monomer to obtain a urethane (meth) acrylate resin containing 1.26% by weight of the isocyanate group (a-9).

Synthesis Example 10

The same system as the synthesis example 1, was charged with 356 parts of polymethylene polyphenyl polyisocyanate (Nippon Polyurethane Industry Co., Ltd.) and 0.13 parts of dibutyltin dilaurate, then a mixture solution of 293 parts of 2-hydroxyethyl methacrylate and 0.32 parts of monomethyl ether hydroquinone was dropped for 40 minutes with stirring, under air atmosphere and heating condition. The temperature was maintained at 85 to 95° C. to react. The reaction was traced by an infrared absorption spectrometry and the end point was determined by the constant absorption of an isocyanate group (at about 2250 cm$^{-1}$). A time taken to terminate the reaction was 3 hours. The content of the isocyanate group existing in the urethane (meth) acrylate before it is diluted by a polymerizable monomer was 1.98% by weight, an equivalent weight of an ethylenically unsaturated group was 288 g/eq. After that, it was diluted by 350 parts of a styrene monomer to obtain a urethane (meth) acrylate resin containing 1.29% by weight of the isocyanate group (a-10).

Synthesis Example 11

The same system as the synthesis example 1, was charged with 309 parts of isophorone diisocyanate and 0.13 parts of dibutyltin dilaurate, then a mixture solution of 294 parts of polyester polyol (P-1), 47 parts of 2-hydroxyethyl methacrylate, 217 parts of a styrene monomer and 0.32 parts of monomethyl ether hydroquinone was dropped for 40 minutes with stirring, under air atmosphere and heating condition. The temperature was maintained at 85 to 95° C. to react. The reaction was traced by an infrared absorption spectrometry and the end point was determined by the constant absorption of an isocyanate group (at about 2250 cm$^{-1}$). A time taken to terminate the reaction was 3 hours. The content of the isocyanate group existing in the urethane (meth) acrylate before it is diluted by a polymerizable monomer was 1.90% by weight, an equivalent weight of an ethylenically unsaturated group was 1804 g/eq. After that, it was diluted by 350 parts of a styrene monomer to obtain a urethane (meth) acrylate resin containing 1.24% by weight of the isocyanate group (a-11).

Synthesis Example 12

The same system as the synthesis example 1, was charged with 393 parts of isophorone diisocyanate and 0.13 parts of dibutyltin dilaurate, then a mixture solution of 87 parts of 1,3-propanediol, 169 parts of 2-hydroxyethyl methacrylate and 0.32 parts of monomethyl ether hydroquinone was dropped for 40 minutes with stirring, under air atmosphere and heating condition. The temperature was maintained at 85 to 95° C. to react. The reaction was traced by an infrared absorption spectrometry and the end point was determined by the disappeared absorption of an isocyanate group (at about 2250 cm$^{-1}$). A time taken to terminate the reaction was 3 hours. The content of the isocyanate group existing in the urethane (meth) acrylate before it is diluted by a polymerizable monomer was 0.00% by weight, an equivalent weight of an ethylenically unsaturated group was 500 g/eq. After that, it was diluted by 350 parts of a styrene monomer to obtain a urethane (meth) acrylate resin containing no isocyanate group (a-12).

Synthesis Example 13

The same system as the synthesis example 1, was charged with 395 parts of isophorone diisocyanate and 0.13 parts of dibutyltin dilaurate, then a mixture solution of 85 parts of 1,3-propanediol, 169 parts of 2-hydroxyethyl methacrylate and 0.32 parts of monomethyl ether hydroquinone, was dropped for 40 minutes with stirring, under air atmosphere and heating condition. The temperature was maintained at 85 to 95° C. to react. The reaction was traced by an infrared absorption spectrometry and the end point was determined by the constant absorption of an isocyanate group (at about 2250 cm$^{-1}$). A time taken to terminate the reaction was 3 hours. The content of the isocyanate group existing in the urethane (meth) acrylate before it is diluted by a polymerizable monomer was 0.10% by weight, an equivalent weight of an ethylenically unsaturated group was 500 g/eq. After that, it was diluted by 350 parts of a styrene monomer to obtain a urethane (meth) acrylate resin containing 0.07% by weight of the isocyanate group (a-13).

Synthesis Example 14

The same system as the synthesis example 1, was charged with 503 parts of hexamethylene diisocyanate and 0.13 parts of dibutyltin dilaurate, then a mixture solution of 347 parts of 2-hydroxyethyl acrylate and 0.32 parts of monomethyl ether hydroquinone was dropped for 40 minutes with air atmosphere heating condition. The temperature was maintained at 85 to 95° C. to react. The reaction was traced by an infrared absorption spectrometry and the end point was determined by the constant absorption of an isocyanate group (at about 2250 cm$^{-1}$). A time taken to terminate the reaction was 3 hours. The content of the isocyanate group in the urethane (meth) acrylate before it is diluted by a polymerizable monomer was 14.77% by weight, an equivalent weight of an ethylenically unsaturated group was 284 g/eq. After that, it was diluted by 150 parts of a styrene monomer to obtain a urethane (meth) acrylate resin containing 12.55% by weight of the isocyanate group (a-14).

Synthesis Example 15

The same system as the synthesis example 1, was charged with 454 parts of bisphenol A type of epoxy resin (JER "#1004"), 85 parts of mathacrylic acid, 1.65 parts of 2-methylimidazole and 0.3 parts of monomethyl ether hydroquinone with stirring, under air atmosphere and heating condition to maintain 110 to 120° C. of a temperature to react it for 10 hours. After that, it was diluted by 460 parts of a styrene monomer to obtain an epoxy acrylate resin wherein an equivalent weight of an ethylenically unsaturated group was 549 g/eq (a-15).

Synthesis Example 16

A stainless-steal reaction vessel equipped with a stirring device, a heating device, a thermometer, a fractionally distilling equipment, a nitrogen gas introduction tube, was charged with 360 parts of phthalic anhydride, 282 parts of fumaric acid, 90 parts of ethylene glycol, 399 parts of propylene glycol, then a polycondensation reaction was proceeded under nitrogen atmosphere, with stirring at 210° C., for 11 hours. After that, it was diluted by 430 parts of a styrene monomer to obtain an unsaturated polyester resin wherein an equivalent weight of an ethylenically unsaturated group was 411 g/eq (a-16).

Synthesis Example 17

The same system as the synthesis example 1, was charged with 397 parts of isophorone diisocyanate and 0.13 parts of dibutyltin dilaurate, then a mixture solution of 84 parts of 1,3-propanediol, 169 parts of 2-hydroxyethyl methacrylate and 0.32 parts of monomethyl ether hydroquinone, was dropped for 40 minutes with stirring, under air atmosphere and heating condition. The temperature was maintained at 85 to 95° C. to react. The reaction was traced by an infrared absorption spectrometry and the end point was determined by the constant absorption of an isocyanate group (at about 2250 cm$^{-1}$). A time taken to terminate the reaction was 3 hours. The content of the isocyanate group existing in the urethane (meth) acrylate before it is diluted by a polymerizable monomer was 0.41% by weight, an equivalent weight of an ethylenically unsaturated group was 500 g/eq. After that, it was diluted by 350 parts of a styrene monomer to obtain a urethane (meth) acrylate resin containing 0.26% by weight of the isocyanate group (a-17).

Synthesis Example 18

The same system as the synthesis example 1, was charged with 377 parts of isophorone diisocyanate and 0.13 parts of dibutyltin dilaurate, then a mixture solution of 105 parts of 1,6-hexanediol (Ube Industries, Ltd.), 167 parts of 2-hydroxyethyl methacrylate and 0.32 parts of monomethyl ether hydroquinone was dropped for 40 minutes with stirring, under air atmosphere and heating condition. The temperature was maintained at 85 to 95° C. to react. The reaction was traced by an infrared absorption spectrometry and the end point was determined by the constant absorption of an isocyanate group (at about 2250 cm$^{-1}$). A time taken to terminate the reaction was 3 hours. The content of the isocyanate group existing in the urethane (meth) acrylate before it is diluted by a polymerizable monomer was 2.08% by weight, an equivalent weight of an ethylenically unsaturated group was 505 g/eq. After that, it was diluted by 350 parts of a styrene monomer to obtain a urethane (meth) acrylate resin containing 1.35% by weight of the isocyanate group (a-18).

Synthesis Example 19

The same system as the synthesis example 1, was charged with 358 parts of a trimer of isophorone diisocyanate (Evonik Industries, VESTANT T 1890) and 0.13 parts of dibutyltin dilaurate to solve them with stirring, under air atmosphere and heating condition and then a mixture solution of 106 parts of 2-hydroxyethyl methacrylate, 186 parts of pentaerythritol triacrylate (TOAGOSEI CO., LTD., ARONIX M-305) and 0.32 parts of monomethyl ether hydroquinone was dropped for 40 minutes. The temperature was maintained at 85 to 95° C. to react. The reaction was traced by an infrared absorption spectrometry and the end point was determined by the constant absorption of an isocyanate group (at about 2250 cm$^{-1}$). A time taken to terminate the reaction was 3 hours. The content of the isocyanate group existing in the urethane (meth) acrylate before it is diluted by a polymerizable monomer was 2.01% by weight, an equivalent weight of an ethylenically unsaturated group was 234 g/eq. After that, it was diluted by 350 parts of a styrene monomer to obtain a urethane (meth) acrylate resin containing 1.31% by weight of the isocyanate group (a-19).

Synthesis Example 20

The same system as the synthesis example 1, was charged with 405 parts of phenol novolac type of epoxy resin (DIC, "N-740"), 195 parts of methacrylic acid, 1.65 parts of 2-methylimidazole and 0.3 parts of monomethyl ether hydroquinone was maintained at 110 to 120° C. to react them under air atmosphere with stirring and heating for 10 hours. After that, it was diluted by 400 parts of a styrene monomer to obtain an epoxy acrylate resin wherein an equivalent weight of an ethylenically unsaturated group is 264 g/eq (a-20).

The Examples 1 to 13, the reference Examples 1 to 4 and the comparative examples 1 to 4 are shown in tables 1 to 3. Methyl methacrylate was used for controlling a viscosity. The following each evaluation results are shown in tables 4 to 6. The reference Example 4 is a urethane (meth) acrylate (Japan U-Pica Company, Ltd., "U-Pica 8921") wherein polyester polyol is used as the alcohol compound. The Examples 14 to 16, the comparative example 5 are shown in tables 7 and 8. The following each evaluation results are shown in tables 10 and 11. The comparative example 5 is those corresponding to the Example 16.

TABLE 1

|  |  | Exa. 1 | Exa. 2 | Exa. 3 | Exa. 4 | Exa. 5 | Exa. 6 | Exa. 7 |
| --- | --- | --- | --- | --- | --- | --- | --- | --- |
| Urethane acrylate resin | Type | a-1 | a-2 | a-3 | a-4 | a-5 | a-6 | a-7 |
|  | Parts by weight | 75 | 85 | 81 | 70 | 74 | 100 | 100 |
| Methyl methacrylate | Parts by weight | 25 | 15 | 19 | 30 | 26 | 0 |  |
| Viscosity (25° C.) | mPa · s | 95 | 97 | 270 | 180 | 88 | 110 | 306 |
| Content of isocyanate group | Percent by weight | 1.03 | 1.17 | 1.10 | 1.16 | 0.10 | 4.45 | 7.53 |

TABLE 2

|  |  | Exa. 8 | Exa. 9 | Exa. 10 | Exa. 11 | Exa. 12 | Exa. 13 |
| --- | --- | --- | --- | --- | --- | --- | --- |
| Urethane acrylate resin | Type | a-8 | a-9 | a-10 | a-11 | a-12 | a-1 |
|  | Parts by weight | 92 | 85 | 77 | 56 | 35 | 40 |
|  | Type |  |  |  | a-8 | a-1 |  |
|  | Parts by weight |  |  |  | 14 | 40 |  |
| Epoxy acrylate resin | Type |  |  |  |  |  | a-15 |
|  | Parts by weight |  |  |  |  |  | 40 |
| Methyl methacrylate | Parts by weight | 8 | 15 | 23 | 30 | 25 | 20 |
| Viscosity (25° C.) | mPa · s | 310 | 360 | 210 | 105 | 99 | 297 |
| Content of isocyanate group | Percent by weight | 1.23 | 1.07 | 0.99 | 0.88 | 0.55 | 0.55 |

TABLE 3

|  |  | Com. 1 | Ref. 1 | Ref. 2 | Com. 2 | Com. 3 | Ref. 3 | Ref. 4 | Com. 4 |
| --- | --- | --- | --- | --- | --- | --- | --- | --- | --- |
| Urethane acrylate resin | Type | a-12 | a-13 | a-14 |  |  | a-1 | U-Pica8921 |  |
|  | Parts by weight | 75 | 74 | 94 |  |  | 100 | 100 |  |
| Epoxy acrylate resin | Type |  |  |  | a-15 |  |  |  |  |
|  | Parts by weight |  |  |  | 100 |  |  |  |  |
| Unsaturated polyester resin | Type |  |  |  |  | a-16 |  |  |  |
|  | Parts by weight |  |  |  |  | 100 |  |  |  |
| Bisphenol type epoxy resin | Parts by weight |  |  |  |  |  |  |  | 100 |
| Methyl methacrylate |  | 25 | 26 | 6 |  |  |  |  |  |
| Viscosity (25° C.) |  | 100 | 110 | 144 | 318 | 283 | 1800 | 468 | 35000 |
| Content of isocyanate group | Percent by weight | 0.00 | 0.05 | 11.80 | 0.00 | 0.00 | 1.37 | 0.01 | 0.00 |

TABLE 4

| Item | Unit | Exa. 1 | Exa. 2 | Exa. 3 | Exa. 4 | Exa. 5 | Exa. 6 | Exa. 7 |
| --- | --- | --- | --- | --- | --- | --- | --- | --- |
| Workability |  | ◎ | ◎ | ◎ | ◎ | ◎ | ◎ | ○ |
| Compressive strength | MPa | 521 | 498 | 501 | 493 | 506 | 499 | 486 |
| Compressive modulus | GPa | 40 | 39 | 41 | 36 | 40 | 40 | 40 |
| Interlaminar shear strength | MPa | 73 | 74 | 71 | 74 | 72 | 72 | 69 |
| Tensile strength | MPa | 578 | 583 | 569 | 546 | 573 | 568 | 577 |
| Tensile modulus | GPa | 48 | 48 | 49 | 493 | 48 | 48 | 486 |
| Flexural strength | MPa | 837 | 821 | 802 | 799 | 824 | 792 | 801 |

TABLE 4-continued

| Item | Unit | Exa. 1 | Exa. 2 | Exa. 3 | Exa. 4 | Exa. 5 | Exa. 6 | Exa. 7 |
|---|---|---|---|---|---|---|---|---|
| Flexural modulus | GPa | 49 | 47 | 49 | 49 | 49 | 49 | 48 |
| With or without of void | | ○ | ○ | ○ | ○ | ○ | ○ | ○ |
| Deflection temperature under load of casting plate | °C. | 106 | 104 | 113 | 88 | 106 | 107 | 103 |

TABLE 5

| Item | Unit | Exa. 8 | Exa. 9 | Exa. 10 | Exa. 11 | Exa. 12 | Exa. 13 |
|---|---|---|---|---|---|---|---|
| Workability | | ○ | ○ | ⊚ | ⊚ | ⊚ | ⊚ |
| Compressive strength | MPa | 494 | 511 | 489 | 502 | 520 | 468 |
| Compressive modulus | GPa | 41 | 37 | 40 | 35 | 40 | 40 |
| Interlaminar shear strength | MPa | 71 | 72 | 62 | 75 | 70 | 68 |
| Tensile strength | MPa | 581 | 579 | 566 | 588 | 581 | 572 |
| Tensile modulus | GPa | 50 | 49 | 50 | 49 | 48 | 49 |
| Flexural strength | MPa | 857 | 843 | 788 | 832 | 831 | 807 |
| Flexural modulus | GPa | 50 | 49 | 50 | 46 | 48 | 49 |
| With or without of void | | ○ | ○ | ○ | ○ | ○ | ○ |
| Deflection temperature under load of casting plate | °C. | 121 | 96 | 133 | 67 | 107 | 107 |

TABLE 6

| Item | Unit | Com. 1 | Ref. 1 | Ref. 2 | Com. 2 | Com. 3 | Ref. 3 | Ref. 4 | Com. 4 |
|---|---|---|---|---|---|---|---|---|---|
| Workability | | ⊚ | ⊚ | ⊚ | Δ | ⊚ | X | ○ | X |
| Compressive strength | MPa | 390 | 386 | 424 | 354 | 208 | 432 | 399 | 488 |
| Compressive modulus | GPa | 40 | 39 | 37 | 35 | 33 | 36 | 38 | 35 |
| Interlaminar shear strength | MPa | 53 | 51 | 61 | 51 | 32 | 64 | 55 | 68 |
| Tensile strength | MPa | 568 | 538 | 533 | 549 | 438 | 511 | 554 | 571 |
| Tensile modulus | GPa | 44 | 45 | 43 | 50 | 50 | 46 | 50 | 45 |
| Flexural strength | MPa | 793 | 779 | 751 | 710 | 540 | 720 | 721 | 798 |
| Flexural modulus | GPa | 49 | 49 | 48 | 48 | 46 | 48 | 44 | 46 |
| With or without of void | | ○ | ○ | ○ | ○ | ○ | Δ | ○ | X |
| Deflection temperature under load of casting plate | °C. | 106 | 106 | 69 | 108 | 68 | 105 | 113 | 63 |

TABLE 7

| | | Exa. 14 | Exa. 15 | Exa. 16 |
|---|---|---|---|---|
| Urethane acrylate resin | Type | a-17 | a-18 | a-19 |
| | Parts by weight | 80 | 75 | 85 |
| Methyl methacrylate | Parts by weight | 20 | 25 | 15 |
| Viscosity (25° C.) | mPa·s | 213 | 101 | 150 |
| Content of isocyanate group | Percent by weight | 0.21 | 1.01 | 1.15 |

TABLE 8

| | | Com. 5 |
|---|---|---|
| Urethane acrylate resin | Type | a-20 |
| | Parts by weight | 100 |
| Methyl methacrylate | Parts by weight | — |
| Viscosity (25° C.) | mPa·s | 187 |
| Content of isocyanate group | Percent by weight | 0 |

TABLE 9

| Item | Unit | Exa. 14 | Exa. 15 | Exa. 16 |
|---|---|---|---|---|
| Workability | | ⊚ | ⊚ | ⊚ |
| Compressive strength | MPa | 484 | 528 | 454 |
| Compressive modulus | GPa | 37 | 36 | 39 |
| Interlaminar shear strength | MPa | 66 | 73 | 55 |
| Tensile strength | MPa | 554 | 587 | 523 |
| Tensile modulus | GPa | 49 | 48 | 53 |
| Flexural strength | MPa | 802 | 834 | 792 |
| Flexural modulus | GPa | 49 | 48 | 51 |
| With or without of void | | ○ | ○ | ○ |
| Deflection temperature under load of casting plate | °C. | 105 | 93 | 173 |

TABLE 10

| Item | Unit | Com. 5 |
|---|---|---|
| Workability | | ⊚ |
| Compressive strength | MPa | 311 |
| Compressive modulus | GPa | 36 |
| Interlaminar shear strength. | MPa | 41 |
| Tensile strength | MPa | 468 |
| Tensile modulus | GPa | 47 |

TABLE 10-continued

| Item | Unit | Com. 5 |
|---|---|---|
| Flexural strength | MPa | 602 |
| Flexural modulus | GPa | 48 |
| With or without of void |  | ○ |
| Deflection temperature under load of casting plate | ° C. | 143 |

Preparation of a Laminated Plate

After to 150 parts of each resin of the Examples 1 to 13, the Reference Examples 1 to 4 and the Comparative Examples 1 to 3 were added 0.5 parts of 6% cobalt naphthenate as the accelerator, 1.0 parts of a curing agent of methyl ethyl ketone peroxide was formulated and it is impregnated to a plain weave cloth of carbon fibers (Toray Industries, Inc., trade name: "T-6343"), it was molded by a hand lay-up molding. In the Comparative Example 4, to 100 parts of bisphenol F type of epoxy resin (Mitsubishi Chemical Corporation JER807) were added 53 parts of aliphatic polyamine (Mitsubishi Chemical Corporation JER cure ST11) and it was impregnated to mold a laminated plate.

Structure of the laminated plate: 25 cm×25 cm×8 ply, 2 mm of thickness, 40 Vf (volume) % of the content of the carbon fibers. Curing conditions: curing at a room temperature (23° C.)×6 hours, 80° C.×2 hours, 100° C.×2 hours
(Evaluation of Workability)

A time from a beginning of a laminate by a hand lay-up molding to end was measured and it was as a standard of workability. ⊚: ~15 minutes, ○: 15~20 minutes, Δ: 25~30 minutes, x: 30 minutes~.
(Evaluation of Mechanical Properties)

As to each laminated plate, a compressive strength (JIS K 7018), an interlaminar shear strength (JIS K 6911), a flexural strength (JIS K 7074), a tensile strength (JIS K 7113) were measured in reference to each JIS.
(Evaluation of Heat Resistance)

A casting plate of each resin was prepared by the same curing method as the manufacture of the laminated plate, and a deflection temperature under load was measured in reference to JIS.
(Verification as to with or without of Void)

20 cm×2 mm of a cross section surface was observed by the microscope (200 times), it was evaluated by the following standard. ○: 0~3 pieces, Δ: 3~9 pieces, x: 10 or more pieces.

As a result, it was shown that a carbon fiber reinforced plastic using resins of the Examples 1 to 16 wherein a urethane (meth) acrylate compound (A) having isocyanate groups and ethylenically unsaturated groups according to the present invention shown in tables 1, 2 and 7 is contained, has superiorresults in workability and mechanical properties. In particular, a good result was obtained in a compressive strength and an interlaminar shear strength. Moreover, in the Examples 3, 8, 10 and 16, a good result was also obtained in a heat resistance. On the other hand, in the Comparative Examples 1 to 5, it was impossible to obtain a sufficient compressive strength and an interlaminar shear strength.

The invention claimed is:

1. A resin composition for a carbon fiber reinforced plastic comprising a urethane (meth) acrylate compound (A) characterized by being represented by the following chemical formula [Chemical 1]:

 [Chemical 1]

(wherein X is a compound residue having two or more isocyanate groups, M contains at least the following formula [Chemical 2]:

 [Chemical 2]

and M other than the above formula [Chemical 2] is the following formula [Chemical 3]:

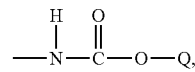 [Chemical 3]

Q is a monoalcohol compound residue containing ethylenically unsaturated groups in the formula, and "n" is 2 to 7), wherein the isocyanate group existing in the urethane (meth) acrylate compound (A) is present at 0.1 to 12 percent by weight.

2. A resin composition for a carbon fiber reinforced plastic comprising a urethane (meth) acrylate compound (A) characterized by being represented by the following chemical formula [Chemical 4]:

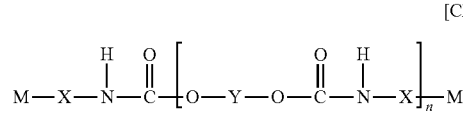 [Chemical 4]

(wherein X is a compound residue having two or more isocyanate groups, Y is an alcohol compound residue having two or more hydroxyl groups, M contains at least the following formula [Chemical 5]:

 [Chemical 5]

and M other than the above formula [Chemical 5] is the following formula [Chemical 6]:

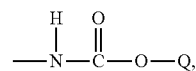 [Chemical 6]

Q is a monoalcohol compound residue containing ethylenically unsaturated groups in the formula, and "n" is 1 to 5000), wherein the isocyanate group existing in the urethane (meth) acrylate compound (A) is present at 0.1 to 12 percent by weight.

3. A resin composition for a carbon fiber reinforced plastic comprising a urethane (meth) acrylate compound (A) according to claim 1, wherein it is a urethane (meth) acrylate produced by reacting a compound having two or more isocyanate groups with a monoalcohol compound containing ethylenically unsaturated groups, or by reacting a compound having two or more isocyanate groups with a monoalcohol compound containing ethylenically unsaturated groups and an alcohol compound having two or more hydroxyl groups, the urethane (meth) acrylate compound (A) being characterized by having an isocyanate group and ethylenically unsaturated groups.

4. A resin composition for a carbon fiber reinforced plastic comprising a urethane (meth) acrylate compound (A) according to claim 2, wherein the alcohol compound having two or more hydroxyl groups is one or more selected from 1,3-propanediol, 1,4-butanediol, 1,5-pentanediol, 1,6-hexanediol.

5. A resin composition for a carbon fiber reinforced plastic comprising a urethane (meth) acrylate compound (A) according to claim 2, wherein the alcohol compound having two or more hydroxyl groups is polyester polyol obtained by the polycondensation of dicarboxylic acid or an ester forming derivative thereof with glycol.

6. A resin composition for a carbon fiber reinforced plastic comprising a urethane (meth) acrylate compound (A) according to claim 2, wherein the alcohol compound having two or more hydroxyl groups is polyester polyol obtained by the polycondensation of one or more selected from terephthalic acid, isophthalic acid, an ester forming derivative thereof, with one or more selected from 1,3-propanediol, 1,4-butanediol, 1,5-pentanediol, 1,6-hexanediol.

7. A resin composition for a carbon fiber reinforced plastic comprising a urethane (meth) acrylate compound (A) according to claim 1, wherein the compound having two or more isocyanate groups is one or more selected from 1,6-hexamethylene diisocyanate, 1,3-bis (isocyanatomethyl) cyclohexane, isophorone diisocyanate, and a prepolymer thereof, polymethylenepolyphenyl polyisocyanate.

8. A resin composition for a carbon fiber reinforced plastic according to claim 1, wherein the resin composition for a carbon fiber reinforced plastic comprises a urethane (meth) acrylate resin (B) characterized by comprising the urethane (meth) acrylate compound (A) and a polymerizable monomer.

9. A resin composition for a carbon fiber reinforced plastic according to claim 8, wherein an isocyanate group existing in the urethane (meth) acrylate resin (B) is present at 0.1 to 8 percent by weight.

10. A resin composition for a carbon fiber reinforced plastic, composed of a thermosetting resin having ethylenically unsaturated groups and a resin composition for a carbon fiber reinforced plastic according to claim 1, wherein an isocyanate group existing in the resin composition is present at 0.1 to 8 percent by weight.

11. A resin composition for a carbon fiber reinforced plastic comprising a urethane (meth) acrylate compound (A) according to claim 2, wherein it is a urethane (meth) acrylate produced by reacting a compound having two or more isocyanate groups with a monoalcohol compound containing ethylenically unsaturated groups, or by reacting a compound having two or more isocyanate groups with a monoalcohol compound containing ethylenically unsaturated groups and an alcohol compound having two or more hydroxyl groups, the urethane (meth) acrylate compound (A) being characterized by having an isocyanate group and ethylenically unsaturated groups.

* * * * *